United States Patent [19]

Comeau

[11] Patent Number: 5,415,758

[45] Date of Patent: May 16, 1995

[54] METHOD AND APPARATUS FOR ELECTRO-ELUTION OF BIOLOGICAL MOLECULES

[75] Inventor: Anne M. Comeau, Newburyport, Mass.

[73] Assignee: Theobald Smith Research Institute, Inc., Boston, Mass.

[21] Appl. No.: 154,985

[22] Filed: Nov. 19, 1993

[51] Int. Cl.⁶ ............................................. C25C 7/02
[52] U.S. Cl. ............................. 204/299 R; 204/289
[58] Field of Search ............ 204/299 R, 180.1, 182.8, 204/288, 289; 435/6, 7.1, 803; 436/501

[56] References Cited

U.S. PATENT DOCUMENTS

| | | | |
|---|---|---|---|
| 3,888,758 | 6/1975 | Saeed | 204/299 |
| 4,000,421 | 12/1976 | Jones et al. | 250/284 |
| 4,340,457 | 7/1982 | Kater | 204/195 |
| 4,545,888 | 10/1985 | Walsh | 204/301 |
| 4,576,702 | 3/1986 | Peck et al. | 204/299 |
| 4,608,147 | 8/1986 | Clad | 204/301 |
| 4,707,233 | 11/1987 | Margolis | 204/182.3 |
| 4,822,470 | 4/1989 | Chang | 204/299 |
| 4,859,302 | 8/1989 | Alfenito | 204/182.8 |
| 4,959,133 | 9/1990 | Adcock | 204/182.8 |
| 4,964,961 | 10/1990 | Brautigam et al. | 204/182.3 |
| 5,102,518 | 4/1992 | Doering et al. | 204/182.8 |

FOREIGN PATENT DOCUMENTS

51-29516  8/1976  Japan .

Primary Examiner—John Niebling
Assistant Examiner—Edna Wong
Attorney, Agent, or Firm—Weingarten, Schurgin, Gagnebin & Hayes

[57] ABSTRACT

The invention includes methods for electro-elution of a biological molecule from a biological sample matrix, the methods including electro-eluting a negatively charged molecule from each of plural individual sample matrices via corresponding plural electric fields which include an electrified anode wire comprising a plurality of serially connected conductive extensions and an electrified cathode wire, wherein each electric field extends from a single conductive anode extension and the cathode wire.

35 Claims, 4 Drawing Sheets

METHOD AND APPARATUS FOR ELECTRO-ELUTION OF BIOLOGICAL MOLECULES

FIELD OF THE INVENTION

The invention relates in general to isolation of biological molecules from a matrix, and in particular to removal of such molecules by electro-elution.

BACKGROUND OF THE INVENTION

The invention was made in part with U.S. Government support under contract number NO1-HD-8-2917, awarded by the National Institute of Child Health and Human Development (NICHD). Therefore, the U.S. Government has certain rights in the invention.

Isolation of nucleic acids and proteins from electrophoresis gels has been performed according to methods available in the prior art. For example, nucleic acids have been recovered from agarose or acrylamide gels by methods such as diffusion, extrusion by compression or crushing of the gel coupled with glass bead recovery, gel dissolution followed by chemical extraction, and electro-elution. Electro-elution is the elution of a charged molecule from a matrix by movement of that molecule within an electric field. Electro-elution methods of the prior art include elution in an electric field onto, e.g., DEAE paper, or into a dialysis membrane. Recovery of the eluted molecule from the paper or membrane may be difficult due to irreversible binding, and may result in degradation, contamination or loss of the end product.

Prior art electro-elution methods also may result in selective recovery of molecules based on size, charge, or other properties. Such methods are particularly inefficient where the sample includes only a minute amount of the biological molecule. Furthermore, transfer of the eluted product from the paper or membrane to a concentrator, or concentration of the product from a relatively large volume involves the risk of loss of the end product. Simultaneous processing of multiple samples, e.g., hundreds, according to prior art electro-elution methods, is difficult and cumbersome.

It is an object of the invention to provide for selective recovery of charged molecules from impure samples such as body fluids. Another object is to provide for highly quantitative recovery of biological molecules. Another object of the invention is to allow for recovery of biological molecules from a number of samples simultaneously, thus saving time and effort and providing for subsequent simultaneous processing of the samples. Yet another object of the invention is to provide for simultaneous recovery of exceedingly small amounts of biological molecules from multiple samples. Another object of the invention is to avoid the risk of loss of the eluted product by providing an end product preparation which does not require concentration from a large volume or, in some diagnostic assays, does not require further purification after electro-elution.

SUMMARY OF THE INVENTION

The invention is based on the electro-elution of charged biological molecules from large numbers of biological samples simultaneously, and features apparatuses and methods for accomplishing this. All methods and devices of the invention include two electrode wires, an anode and a cathode electrode wire, one electrode wire of which includes plural serial conductive extensions. The invention provides for isolation of a biological molecule from a sample matrix into an individualized compartment containing a solution that is readily accessible for assay.

The invention features an electro-elution apparatus comprising plural sample chambers, each sample chamber containing an eluant solution; an anode wire and a cathode wire, wherein one of the anode or cathode wires comprises a plurality of serially connected conductive extensions, and each conductive extension extends into a corresponding sample chamber, and wherein each sample chamber defines a flow path for flow of electrolytes between cathode and anode wires, wherein the plural sample chambers are simultaneously accessible for simultaneous removal of the eluate solutions. As used herein, "serially connected conductive extensions" refers to conductive electrode extensions which are arranged serially rather than in parallel such that electricity runs from an electrical source and through each conductive extension in turn rather than to each extension independently.

Preferably, the apparatus further includes a buffer reservoir for containing the plural sample chambers, wherein each sample chamber includes upper and lower portions, the lower portion comprising barrier means for allowing electrolyte flow but preventing liquid exchange between each chamber and the reservoir.

Preferably, the anode wire includes the plurality of serially connected conductive extensions for extending into each corresponding sample chamber, and the cathode wire extends into the buffer reservoir.

The invention also features an electro-elution apparatus comprising an anode wire comprising a plurality of serially connected conductive extensions, and a cathode wire.

The apparatus may further include a plurality of sample chambers and a buffer reservoir, wherein each anode wire conductive extension extends into a sample chamber and the cathode wire extends beneath the sample chambers into the buffer reservoir, wherein each sample chamber defines a flow path for flow of electrolytes between the cathode wire and each anode wire conductive extension. Because the electric field and thus the flow path is oriented in the cathode to anode direction, i.e., against the flow of gravity, an electro-elution apparatus which includes this embodiment of the invention is particularly useful for easily retrieving multiple samples simultaneously.

Preferably, the sample chamber comprises upper and lower portions, the lower portion including an orifice and a barrier means for allowing electrolyte flow but preventing liquid exchange between each sample chamber and the reservoir through the orifice.

Preferably, each sample chamber defines an internal volume of less than 500 $\mu$l. The apparatus may further include a power supply to which anode wire and cathode wires electrically connect. The apparatus may also include insulated handle means for placing the anode wire such that the anode wire conductive extensions extend into the sample chambers. Preferably, the insulated handle means includes a cover to which the anode wire is structurally attached. The anode wire may further include insulating material wrapped around the wire in the portion of the wire between the conductive extensions.

The invention also includes a method of electro-elution which includes providing plural electric fields using an apparatus comprising plural sample chambers, each sample chamber containing an eluant solution, an anode wire and a cathode wire, wherein one of the anode or cathode wires comprises a plurality of serially connected conductive extensions, and each conductive extension extends into a corresponding sample chamber, and wherein each sample chamber defines a flow path for flow of electrolytes between cathode and anode wires, wherein the plural sample chambers are simultaneously accessible for simultaneous removal of the eluate solutions; providing corresponding plural individual sample matrices; and simultaneously electro-eluting a charged molecule from each of the plural individual sample matrices into each of corresponding plural individual sample eluants. The terms "eluant" and "eluate" are conventional terms and retain their conventional meaning herein; i e., . "eluant" refers to a solution used in eluting a biological molecule from a sample, and "eluate" refers to a solution obtained by eluting a molecule into an eluant.

Preferably, the method further includes simultaneously recovering the plural individual sample eluates.

The invention also includes a method of electro-elution which includes electro-eluting a negatively charged molecule from each of plural individual sample matrices via corresponding plural electric fields comprising an electrified anode wire comprising a plurality of serially connected conductive extensions and an electrified cathode wire, wherein each electric field extends from a single conductive anode extension and cathode wire.

The invention also includes a method of electro-elution which includes the steps of (a) providing an apparatus including an anode wire comprising a plurality of serially connected conductive extensions and a cathode wire; (b) placing each of plural sample matrices containing a biological molecule between each conductive anode extension and the cathode wire; and (c) providing electricity to the apparatus for a time and under buffer conditions sufficient to simultaneously elute the biological molecule from each sample matrix to form a sample eluate containing the biological molecule.

Preferably, the method further includes the step of (d) collecting the plural sample eluates, e.g., using a multichannel pipetter.

The invention also includes an electro-elution method comprising the steps of (a) providing an electro-elution apparatus comprising a cathode wire extending into a buffer reservoir, an anode wire comprising a plurality of serially connected conductive extensions, and a corresponding plurality of sample chambers, each sample containing an eluant solution, wherein each anode wire conductive extension is extendable into an eluant solution and each sample chamber defines a flow path for flow of electrolytes between the cathode wire in the buffer reservoir and each anode wire conductive extension; (b) placing each of a plurality of sample matrices containing a biological molecule to be eluted into each of the corresponding plurality of sample chambers; (c) providing sufficient electricity to the anode and cathode wires to elute the biological molecule from each of the plural samples into the eluant solution.

The invention also features an electro-elution apparatus comprising first and second electrode wires, wherein the second wire comprises a plurality of serial conductive extensions, each conductive extension being shaped so as to substantially conform to the internal shape of a sample chamber, wherein, upon electrification, the first and second wires are cooperable within each of a plurality of sample chambers simultaneously to define a plurality of electric fields.

The invention also features an electro-elution apparatus comprising (a) first and second electrode wires, each wire including a plurality of conductive extensions, wherein the first and second wires cooperate to form a plurality of pairs of conductive extensions, each pair comprising a first wire conductive extension and a corresponding second wire conductive extension spaced apart so as to define a flowpath in conductive medium for the flow of ions; and (b) a plurality of sample chambers, wherein the members of each pair of conductive extensions extend into a sample chamber.

Preferably, the first electrode wire further comprises plural conductive extensions; the first or second electrode wires further comprises insulating material wrapped around the wire between the conductive extensions; the second electrode wire is shaped such that each second wire conductive extension conforms to the internal shape of each the sample chamber; and each first electrode wire is shaped such that each first wire conductive extension is extendable into a sample chamber without contacting the second wire conductive extension. Preferably, the apparatus further includes a plurality of sample chambers; and at least one of the first and second electrode wires is insulatively adapted so as to allow manual movement of the wire.

The invention also features an electro-elution kit which includes any of the electro-elution apparatuses described above and means for packaging the apparatus.

The invention also features a method of electro-eluting a biological molecule from a sample matrix, which includes the steps of (a) providing an electro-elution apparatus comprising first and second electrode wires electrically connected to an electric power source, wherein at least the second electrode wire includes plural conductive extensions; (b) providing plural sample chambers, each chamber containing a sample matrix comprising said biological molecule and electro-elution buffer solution; (c) placing the first and second wires such that each conductive extension of the second wire extends into a sample chamber of plural sample chambers, the first and second wires being spaced apart so as to define a flow path for ions upon electrification; and (d) eluting the biological molecule by imposing an electric field within each sample chamber between said first and second wires sufficient to elute the biological molecule from the sample matrix into the buffer solution.

The invention also features a method of electro-eluting a biological molecule from a sample matrix, comprising the steps of: (a) providing an electro-elution apparatus comprising first and second electrode wires, wherein the second wire comprises a plurality of serial conductive extensions, each conductive extension being shaped so as to substantially conform to the internal shape of a sample chamber, wherein, upon electrification, the first and second wires are cooperable within each of a plurality of sample chambers simultaneously to define a plurality of electric fields, and providing a plurality of sample chambers, each said chamber containing a sample matrix comprising a biological molecule and a conductive buffer solution, wherein each conductive extension of the second electrode wire is immersed in the solution within the sample chamber; (b) electro-eluting the biological molecule from the sample matrix by imposing an electric field within each the sample chamber between the first and second electrode wires sufficient to elute the biological molecule from the sample matrix into the buffer.

The invention also includes a method of electro-eluting a biological molecule from a sample matrix, comprising the steps of: (a) providing an electro-elution apparatus comprising first and second electrode wires, each wire including a plurality of conductive extensions, wherein the first and second wires cooperate to form a plurality of pairs of conductive extensions, each pair comprising a first wire conductive extension and a corresponding second wire conductive extension spaced apart so as to define a flowpath in conductive medium for the flow of ions; and a plurality of sample chambers, wherein the members of each pair of conductive extensions extend into a sample chamber, wherein each sample chamber further comprises a sample matrix containing the biological molecule and conductive medium; (b) electro-eluting the biological molecule from the sample matrix by imposing an electric field within each the sample chamber between the first and second electrode wires sufficient to elute the biological molecule along the flowpath from the sample matrix into the buffer.

Preferably, in any of the electro-elution methods described above, the eluted biological molecule is selected from the group consisting of nucleic acid and protein. In addition, one or more sample matrix washing steps, e.g., soaking the sample matrix prior to electro-elution so as to remove cellular debris.

Each sample chamber utilized according to the methods described above preferably includes an internal volume of less than 500 $\mu$l, more preferably, less than 250 $\mu$l, and most preferably, less than 100 $\mu$l.

The biological molecule eluted from each sample matrix as described herein may include less than a total of 50 $\mu$g, preferably, less than 10 $\mu$g, more preferably, less than 1-2 $\mu$g.

The invention provides for easy access to a sample chamber for recovery of an electro-eluted molecule, due to the open-ended nature of the sample chambers. In addition, because the inventive methods and devices do not allow for leaking between sample chambers, the danger of cross-contamination of samples is significantly reduced throughout the electro-elution procedure, i.e., before, during and after electro-elution of the sample from the sample matrix. These advantages are especially important for uses contemplated in the invention, i.e., where hundreds of individual samples, e.g., 100, 200–500, or thousands, e.g., 1000, 2000, 3000, 4000–6000, or even up to ten thousand or one-hundred thousand individual samples are analyzed simultaneously.

The invention thus provides for highly quantitative recovery of relatively pure biological molecules from a biological sample. The molecule of interest may be recovered quantitatively from a number of samples simultaneously, thus saving time and effort and providing for subsequent simultaneous processing or analysis of numerous biological molecule samples, if desired. Any number of samples may be subjected to electro-elution simultaneously according to the invention, e.g., a single sample, two samples, tens of samples, and even 100's of samples are conveniently eluted using the devices and methods disclosed herein. The invention thus provides for elution of biological molecules from hundreds of thousands of samples routinely in an efficient and safe manner. The number of simultaneously eluted samples is only limited by the number of sample chambers which are present in a single format. A format may include a single microtiter plate containing numerous individual sample chambers or it may include multiple microtiter plates; the latter format would include serial or parallel electrical connection of the plates to the power supply.

Charged molecules, such as nucleic acids and proteins, may be selectively recovered from impure samples such as body fluids, according to the invention. Exceedingly small amounts of biological molecules may be simultaneously and quantitatively recovered according to the invention. For example, as little as 1 $\mu$g of genomic DNA may be recovered from a single drop, e.g., 25 $\mu$l of blood; as little as 1 $\mu$g of mRNA may be recovered from a single drop of blood; 2.5 $\mu$g of protein may be recovered from 25 $\mu$l serum; or hormones or drugs of interest may be recovered from a sample.

Because the invention provides an end product preparation which does not require concentration from a large volume, the invention avoids risk of loss of the eluted product.

Electro-eluted molecules, e.g., protein or nucleic acids, will be useful, for example, in assays for detection of the presence of a particular protein or nucleic acid in a sample. Such assays are important in the prediction and diagnosis of disease, forensic medicine, epidemiology and public health. For example, electro-eluted genomic DNA may be subjected to hybridization and/or amplification to detect the presence of an infectious virus or a mutant gene in an individual, allowing determination of the probability that the individual will suffer from a disease of infectious or genetic origin. The ability to detect an infectious virus or a mutation in one sample among the hundreds or thousands of samples being screened takes on substantial importance in the early diagnosis or epidemiology of an at-risk population for disease, e.g., the early detection of HIV infection, cancer or susceptibility to cancer, or in the screening of newborns for diseases, where early detection may be instrumental in diagnosis and treatment.

Further objects and advantages of the invention will be apparent in light of the following description and the claims.

DESCRIPTION

Before describing the invention in detail, the drawings will be briefly described.

Drawings

DESCRIPTION OF PREFERRED EMBODIMENTS

The invention features methods and devices for the efficient and quantitative recovery of relatively small amounts of biological molecules from numerous samples by electro-elution.

The sample to be assayed can be in any type of sample, and will generally sample of medical, veterinary, forensic, environmental, nutritional, or industrial significance. Human and animal specimens and body fluids particularly can be assayed by the present method, providing that they contain cells, or particles, e.g., virions, from which nucleic acids can be prepared. Preferred sources include buccal swabs, blood, sperm, other tissue, milk, urine, cerebrospinal fluid, sputum, fecal matter, lung aspirates, throat swabs, genital swabs and exudates, rectal swabs, and nasopharyngeal aspirates.

The invention allows for simultaneous recovery of exceedingly small amounts of biological molecules from, e.g., hundreds of a type of sample in a quantitative manner. Typically 60–100%, and more likely at least 80%, 90% or 95%, of the biological molecule of interest that is present in a biological sample may be recovered according to the invention, even when the sample contains such small amounts as 0.1–10 $\mu g$ of the biological molecule. For example, as much as 1 $\mu g$ of genomic DNA may be recovered from a 25 $\mu l$ blood spot according to the invention. Because the invention allows for elution of the biological molecule into a relatively small volume of liquid, e.g., smaller than 500 $\mu l$, 250 $\mu l$, 100 $\mu l$, and even as small as 5–10 $\mu l$, the invention avoids the risk of loss of the eluted product encountered in concentrating a sample from a relatively large volume.

The biological molecule of interest may be eluted according to the invention from an impure, partially pure, or a pure biological sample. The purity of the sample is not critical to the inventive methods, as molecules of interest may be electro-eluted from even grossly impure samples according to the invention. For example, nucleic acid may be removed from an impure sample of a biological fluid such as blood, saliva, or tissue. If a purer sample is desired, the sample may be treated according to any conventional means known to those of skill in the art prior to undergoing electro-elution according to the invention, e.g., the sample may be processed so as to remove certain impurities from an impure sample prior to electro-elution of the molecule of interest.

Elution methods of the invention may be performed on a sample which is held by any type of matrix, provided the matrix material itself does not possess a strong enough charge to move in an electric field in the same direction as the biological molecule of interest. Thus, the biological sample may be contained within a sample matrix such as paper, textile, e.g., a fragment of an article of clothing, agarose, or acrylamide. One example of a sample and sample matrix according to the invention is a drop of a body fluid, e.g., blood, which has been stored dry on a piece of Schleicher and Schuell #903 paper, the paper routinely used nationwide for the purpose of newborn screening.

For purposes of the following description of the invention, recovery of nucleic acids, e.g., genomic DNA, is described in detail. However, it is to be understood that the invention encompasses recovery of any biological molecule, including nucleic acids, proteins, hormones, and other charged molecules, and a person of ordinary skill in the art will know conventional modifications of the conditions described herein for such an elution. Conditions for electro-elution of proteins and hormones are described respectively in F. M. Ausubel et al., *Current Protocols in Molecular Biology*, Vol. 2, Chap. 10, Greene Publishing *Associates and Wiley Interscience*, NY 1988, and Robbins et al., *Recent Progress in Hormone Research* 14:161, 1957, the contents of both references of which are incorporated herein.

It is also to be understood that although certain elements of the components of the invention, e.g., electrode conductive extensions and sample chambers, are described as being of a particular shape or configuration, any alternative shape or configuration of such elements are encompassed within the scope of the invention.

Figure 1:
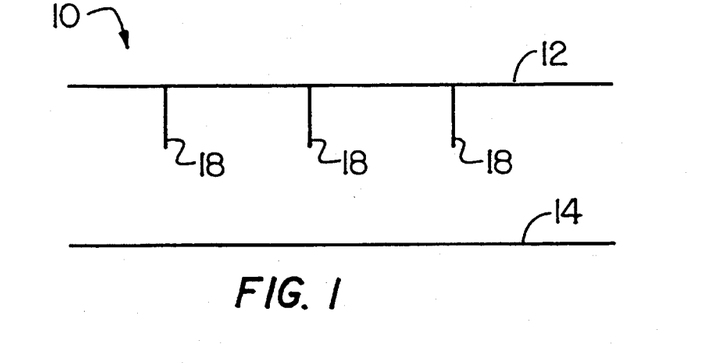
FIG. 1 is an exploded side view of an electro-elution apparatus according to the invention.
Figure 2:
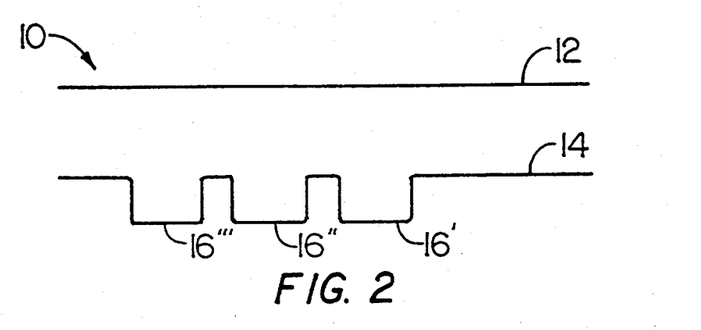
FIG. 2 is an exploded side view of another electro-elution apparatus according to the invention.
Figure 3:
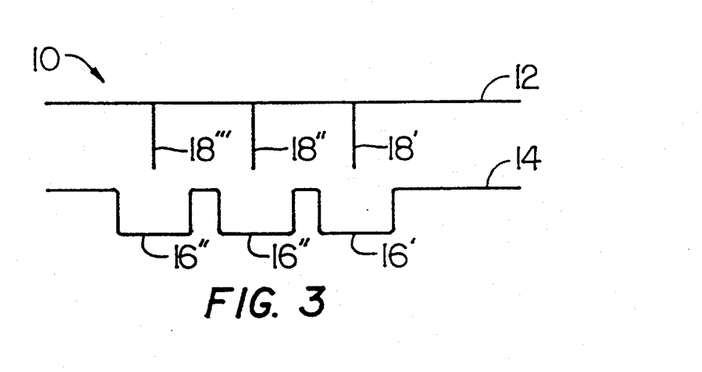
FIG. 3 is an exploded side view of another electro-elution apparatus according to the invention.

Referring to FIGS. 1–4, an electro-elution device 10 of the invention may include first 12 and second 14 electrode wires which cooperate when electrified to create an electric field. In FIG. 1, first electrode wire 12 includes plural serial conductive extensions 18, whereas in FIGS. 2 and 4, second electrode wire 14 contains plural serial conductive extensions 16, each of which is shaped so as to extend into a sample chamber. Alternatively, as shown in FIG. 3, both of the first 12 and second 14 electrode wires may contain plural conductive extensions 18, 16, respectively. Conductive extensions 18 or 16 of the first 12 or second 14 electrode wires are arranged serially rather than in parallel such that electricity runs from an electrical source and through each conductive extension in turn rather than to each extension independently. Thus, the invention provides for use of single cathode and anode wires to create multiple electric fields rather than multiple cathode/anode wire pairs.

Figure 7:
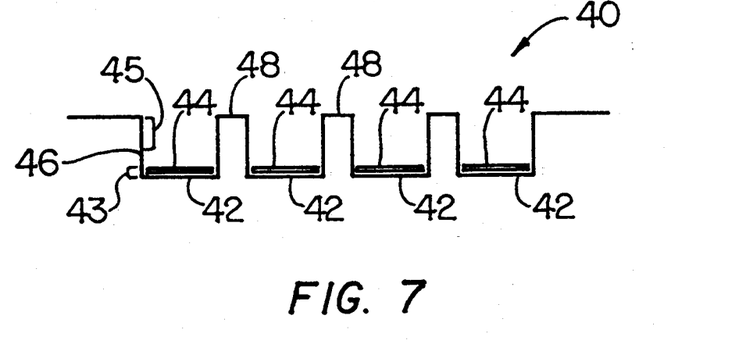
FIG. 7 is a side view of sample chambers in which each chamber contains a sample matrix according to the invention.

In one embodiment of the invention, shown by the combination of first 12 and second 14 electrodes in FIG. 2, at least the second electrode 14 is shaped substantially the same as the sample chamber to which it is to be inserted. That is, if the sample chamber 42 has an internal U-shape, as shown in FIG. 7, then the conductive extensions 16 of second electrode 14 will also possess a substantial U-shape. The substantial similarity of shape between the second wire conductive extensions and the internal sample chamber allows the conductive portion of an electrode to reach the bottom of the sample chamber, below the site where the sample matrix 44, shown in FIG. 7, is likely to rest. According to this embodiment of the invention, the first electrode 12 may be of any shape which, upon electrification of both electrodes, 12, 14, allows for establishment of an electric field between each second wire conductive extension 16 and first wire 12.

Thus, another embodiment of the invention is shown by the combination of first 12 and second 14 electrode wires shown in FIG. 3. In this embodiment, the first electrode wire 12 contains plural serial conductive extensions 18 which possess a shape conducive to extending toward corresponding second wire conductive extensions 16. For example, as shown in FIG. 3, the first wire conductive extensions 18 comprise straight conductive extensions. Thus, when electricity is running through each of first 12 and second 14 wires, e.g., from a cathode and an anode source, respectively, multiple electric fields are created; one electric field between conductive extensions 16' and 18'; another between conductive extensions 16" and 18", etc.

Figure 4:
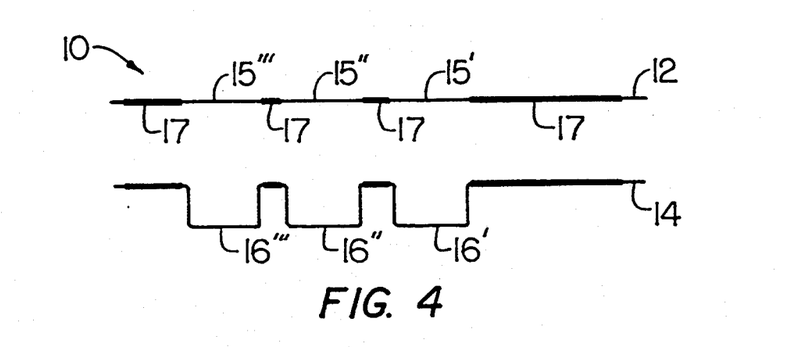
FIG. 4 is an exploded side view of another electro-elution apparatus according to the invention.

An example of an alternative shape for the first electrode wire is shown in FIG. 4. First electrode wire 12 may be a straight wire in which portions 17 of the wire are covered with insulating material and other conductive portions 15 are bare. In this embodiment, the bare conductive portions 15 are not extensions which extend towards the second wire conductive extensions 16, but instead are simply conductive endpoints for each electric field. Thus, when electricity is running through first 12 and second 14 electrode wires, e.g., from a cathode and an anode source, respectively, multiple electric fields are created; one between extension 16' and conductive portion 15'; another between extension 16" and conductive portion 15". In all embodiments of the invention, but particularly in this embodiment, it is critical to immerse the corresponding first wire conductive extension or conductive portion and the second wire conductive extension in a conductive buffer, spaced apart sufficiently to allow for flow of ions along a flowpath defined by the distance between them.

Figure 5:
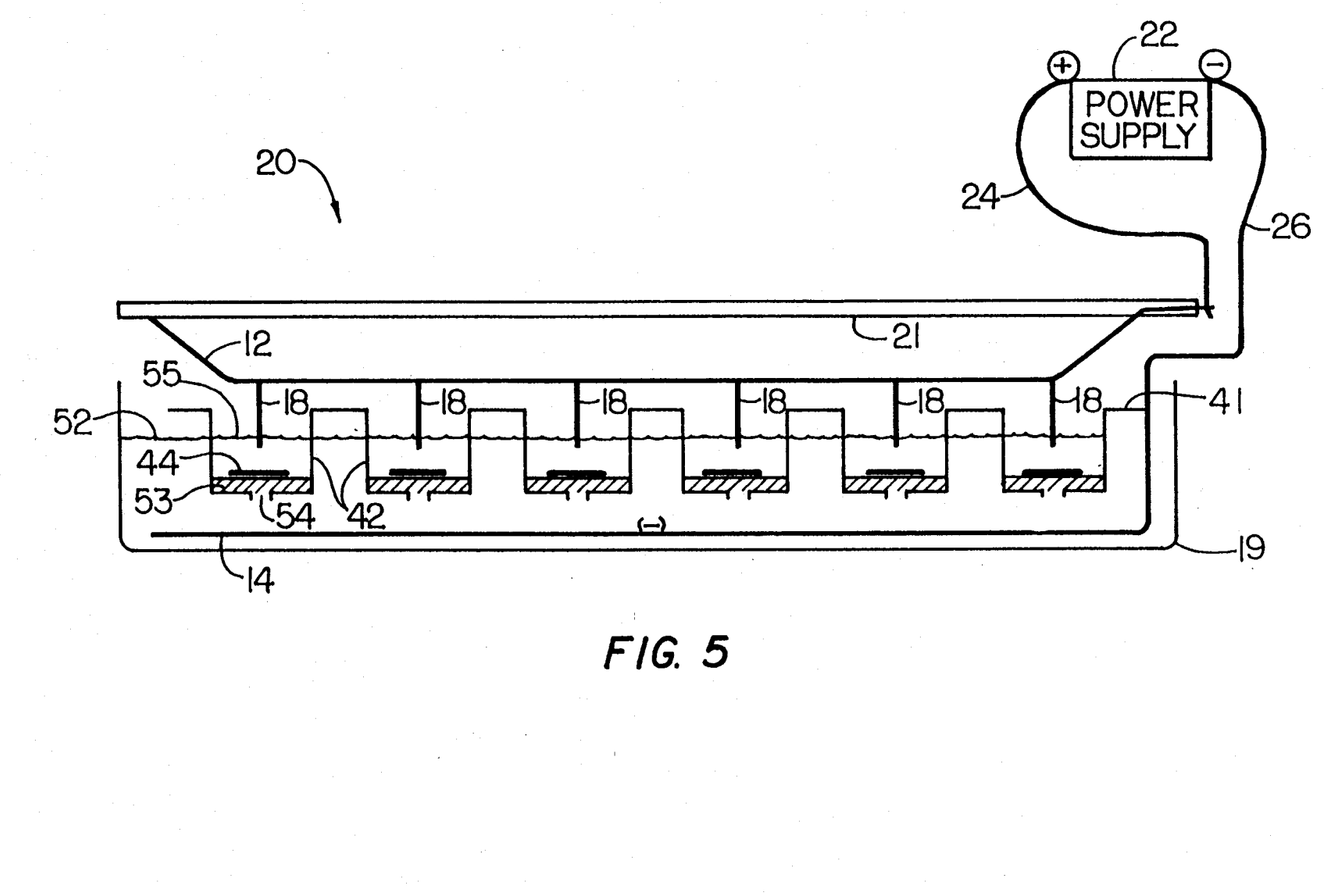
FIG. 5 is a side view of an electro-elution apparatus operable according to the invention.

Referring to FIG. 5, an electro-elution apparatus 20 according to the invention is shown in side view. Plate 41, including plural sample chambers 42, is immersed in buffer 52 within buffer reservoir 19. The bottom of each sample chamber 42 contains barrier 53, which prevents the flow of buffer 55 or 52 through orifice 54 but allows for the flow of electrolytes. Plate 41 may be, for example, a 96-well plastic microtiter dish (Costar Corp., Cambridge, Mass.). A hole may be made in the bottom of each sample chamber of the dish using a multiple hot prong melt which pierces multiple chamber bottoms simultaneously. Alternatively, plate 41 may be purchased as a plate with holes already punched (Dynatech Laboratories, Inc., Chantilly, Va.).

Sample matrix 44, containing the biological sample and thus the biological molecule to be eluted, may lie on top of barrier 53 or may be embedded in barrier 53, e.g., if the barrier is a substance which allows for flow of the biological molecule therethrough. Examples of this type of barrier include but are not limited to agarose or polyacrylamide. For example, the sample matrix may be embedded in an acrylamide plug as it hardens in the bottom of the sample chamber. The purpose of the barrier is to establish a boundary between buffer 52 contained within reservoir 19, i.e., buffer 52 will be negatively charged once cathode electrode wire 14 is electrified, and each sample solution 55 contained in individual sample chambers 42. Barriers which are alternatives to gel-like barriers include but are not limited to membrane barriers which prevent exchange of buffer 52 with solution 55, but allow for the flow of electrolytes, when subjected to an electric field. An example of such a membrane is the BT1 membrane (Schleicher & Schuell, Keene, N.H.). Sample solution 55 within each sample chamber is preferably the same buffer as buffer 52 or a similar buffer. These buffers may differ somewhat in content, e.g., a higher Tris-base molarity may be used in sample chamber buffer 55 such that, after electro-elution, the final pH approaches neutrality rather than acidity. Apparatus 20 also includes first and second electrode wires, which in FIG. 5 are depicted as anode (+) and cathode (−) electrode wires 12, 14, respectively. Anode wire 12 includes plural serial conductive extensions 18, each of which extends into the solution 55 contained within a sample chamber 42. Anode wire 12 is attached to safety lid 21, which is made of a nonconductive material and thus protects the user from the danger of electrocution during use of the apparatus. Anode and cathode wires 12 and 14, respectively, are electrically connected to leads 24 and 26, respectively, which in turn lead to power supply 22 as the electrical source.

In operation, the apparatus 20 of FIG. 5 operates as follows for electro-elution of a negatively charged biological molecule such as nucleic acid. For electro-elution of other types of charged molecules, appropriate conventional modifications may be made, such as reversal of the electric field. Each sample matrix 44 is placed in each of a sample chamber 42 either on top of or embedded within barrier 53, as described above. Microtiter dish 41, each sample chamber of which contains orifice 54, is partially immersed in buffer 52 contained within reservoir 19. Dish 41, containing barrier 53, is immersed only to the point where buffer 52 does not flow over the edges of dish 41 and into the sample chambers. Buffer 55 is aliquotted into all wells of dish 41 and anode wire 12 is then positioned such that the conductive extensions 18 extend into solution 55 in the sample chambers 42. In practice, this positioning involves placing lid 21 such that it rests on the top edges of reservoir 19. Power source 22 is then turned on to deliver electricity along leads 24, 26 to anode and cathode wires 12, 14, respectively. Representative conditions for electro-elution of nucleic acid include constant voltage within the range of 10–100 volts, preferably 25 volts, and 2–100 milli-amps, preferably 5–10 milli-amps, are delivered to the apparatus. Electrification of the anode and cathode wires creates a negatively charged environment in buffer 52 within reservoir 19 and a positively charged environment in each sample chamber solution 55. The opposing positive and negative charges creates an electric field between each anode conductive extension 18 and the cathode wire 14 through orifice 54. Thus, flow of electrolytes is permitted through orifice 54 and between the electrode wires. Because the sample matrix containing the biological sample is positioned between anode extension 18 and cathode wire 14 and thus within the electric field, negatively charged biological molecules contained within the biological sample, e.g., nucleic acids, are carried along the electric field towards the positive electrode. The negatively charged biological molecules are thus eluted from the sample matrix into solution 55. The duration of electro-elution may be from 30 seconds to 60 minutes, ideally the duration will be between 1 and 15 minutes. Electro-elution may be followed immediately by a 15 second reversal of polarity to remove nucleic acid or protein from the anode, leaving it in solution 55.

Once the negatively charged biological molecule has been eluted into solution 55, solution 55 in each sample chamber may be collected for further analysis or storage using a multichannel pipetter (Dynatech, Chantilly, Va.) using aeroseal tips to prevent specimen cross-contamination (United Scientific Supply, Quincy, Mass.). A significant advantage of this aspect of the invention is found in the orientation of the electric field. Because the direction of the electric field is upward with respect to gravity, as shown in FIG. 5, the plural sample solutions 55 are directly accessible for multichannel pipetting. Thus, multiple samples may be collected simultaneously according to the invention.

Figure 6:
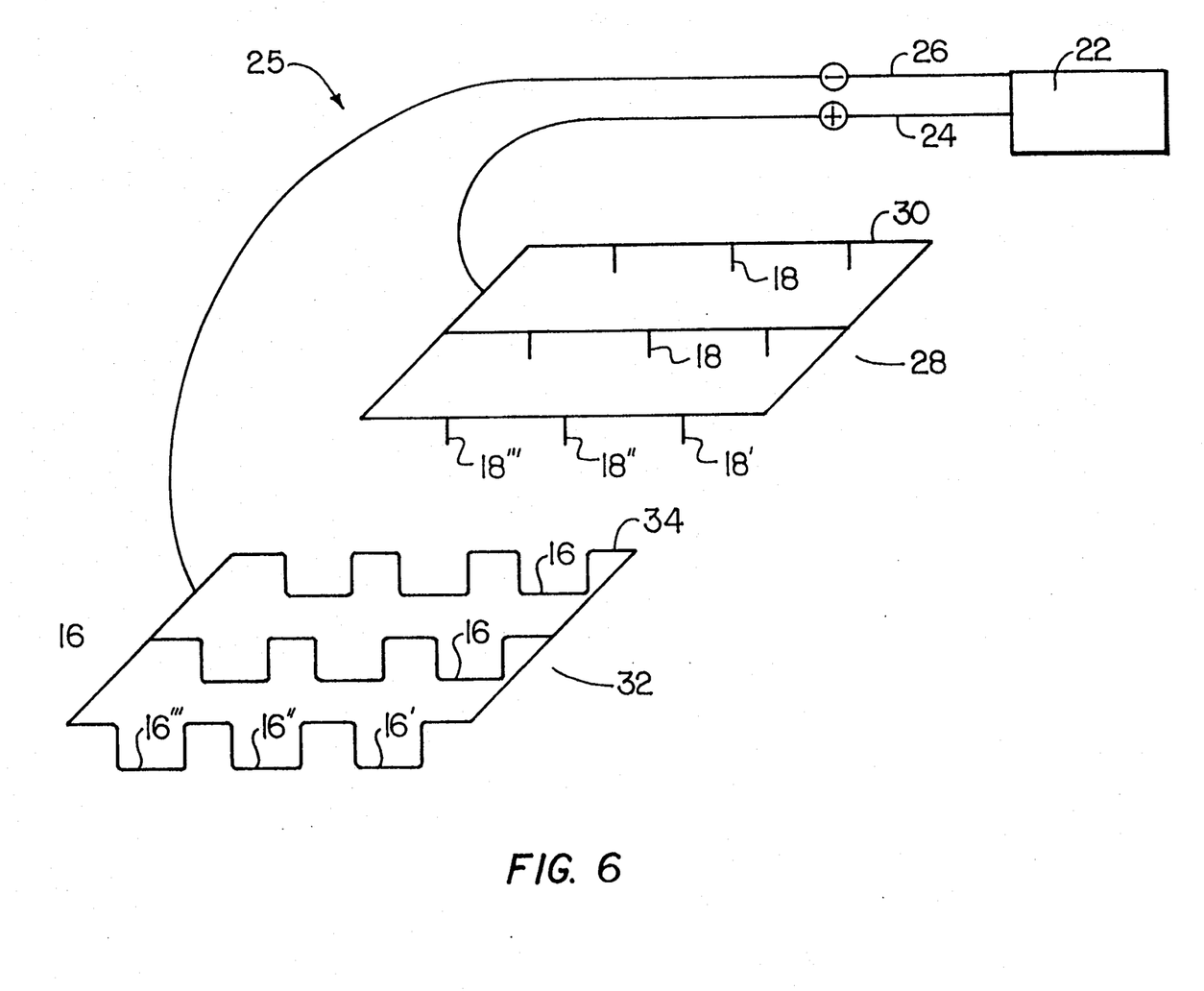
FIG. 6 is a perspective view of an electro-elution apparatus according to the invention which includes an anode, a cathode in a sample grid format.

Referring to FIG. 6, an electro-elution apparatus 25 of the invention is shown in perspective view. First electrode wire 24, an anode wire in FIG. 4, and second electrode wire 26, a cathode wire, are shown electrically connected to power source 22. The operable portion of wire 24 for purposes of the invention is grid 28, which includes numerous conductive extensions 18 arranged serially and extending vertically from parallel horizontal conductive wires 30. Similarly, the operable portion of wire 26 is grid 32, which includes numerous conductive extensions 16 arranged serially and extending vertically in a U-shape from parallel horizontal wires 34. Thus, when electricity is passing through anode wire 24 and cathode wire 26, and grids 28 and 32 are aligned with respect to each other such that each pair of conductive extensions 16', 18' and 16", 18", etc is immersed in a sample chamber containing conductive buffer, an electric field will be established between each pair of conductive extensions 16', 18' and 16", 18". Grids 28 and 32 may be of any shape or configuration, as long as serial transfer of electricity is possible through each of the cathode and anode wires, and the corresponding conductive portions may be aligned.

A sample chamber according to the invention will have an internal shape which allows the sample matrix to rest low enough such that it may be immersed in or overlaid with a conductive buffer. Optimally, numerous sample chambers will be arranged in a single line or grid configuration which corresponds to the line or grid configuration of the first and second electrode wires. If fewer samples are to be subjected to electro-elution, then a grid configuration need not be used; instead a single line configuration of sample chambers may be used, depending upon the number of samples available. Referring to FIG. 7, in which a plurality of sample chambers 40 are shown in side-view, the chambers may be configured in a generally U-shape, each chamber 42 having an a lower volume portion 43 which includes the bottom of the chamber where the sample matrix 44 generally rests, a transition volume portion 46, and an upper volume portion 45. A connecting portion 48 serves to join adjoining chambers and comes into contact with insulated portions of first and second electrode wires when the uninsulated conductive portions of the wires are immersed in conductive buffer.

For electro-elution according to this aspect of the invention, the sample wells will include a conductive buffer which will provide for flow of electrolytes along an electrolyte flowpath defined by the distance within a sample chamber between the cathode and the anode wires. The conductive buffer may be in liquid or semi-liquid form, e.g., an electrophoretic running buffer, or a gel-like substance, such as agarose or acrylamide, hydrated with a running buffer. Optimally, the entire volume of the sample chamber 42, including the upper, transition, and lower volume portions 45, 46, and 43, respectively, are filled with running buffer. If desired, a combination of gel and running buffer may fill the chambers, such that the sample is immersed and held in position in the lower volume portion by solidified gel, and the gel is in turn covered with liquid running buffer such that the transition volume 46 and even the upper volume 45 is filled. Use of a conductive gel in this manner reduces the amount of liquid in which the biological molecule is recovered.

The distance between the anode and cathode wires will vary depending upon the size of the apparatus. For a microtiter format, the optimal distance will be in the range of 1 mm–16 mm, and especially 5–10 mm.

The anode and cathode leads 24, 26 of the power source 22 can be seen in FIG. 6. For identification, positive and negative leads are preferably insulated in red and black, respectively. Such leads are typically insulated with nonconductive finger grips for plugging into the power supply, and are insulated with a nonconductive sheath over that portion of the lead which extends from the power supply to the operative ends 28 and 32. However, because the invention encompasses simultaneous serial conductive extensions which extend from a single lead, portions of the lead which lie between a pair of conductive extensions on one lead may be insulated also. This prevents electric shock to the user, e.g., where lid 21 is not present.

Materials which may be used in the apparatus of the invention include but are not limited to the following. The sample chambers and the lid are made of a nonconductive material which does not promote binding of charged molecules to its surface, e.g., plastic. The electrodes are preferably made of platinum.

Figure 8:
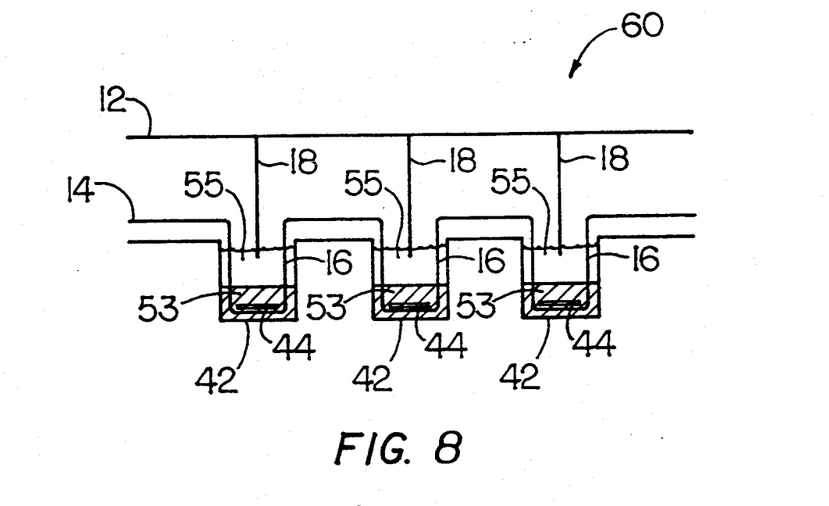
FIG. 8 is a side view of the sample chambers containing sample and first and second electrode wires in position to accomplish electro-elution according to the invention.
Figure 9:
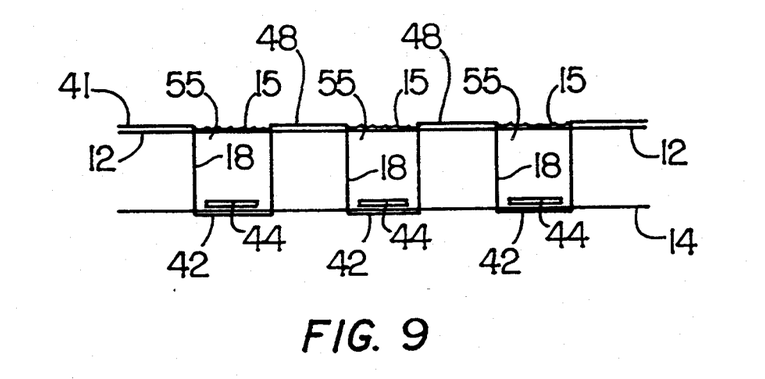
FIG. 9 is a side view of the another apparatus of the invention.

FIGS. 8 and 9 show two alternative embodiments 60, 70 of electro-elution devices according to the invention, each including sample chambers 42, a first electrode wire 12, a second electrode wire 14, sample matrices 44, and running buffer or solution 55.

Thus, in the embodiment shown in FIG. 8, second electrode wire 14 contains multiple conductive extensions 16, each extension conforming to the internal shape of and thus extending into a corresponding sample chamber 42 such that it is beneath the sample matrix 44. A gel plug hydrated with electrophoretic running buffer 53 fills the lower and transition volumes of the sample chamber. Each conductive extension 16 may be embedded within the gel plug. Optimally, sample matrix 44 will be placed upon the gel plug and thus over the conductive extension 16. The gel plug is then overlaid with enough liquid running buffer 55 to fill the upper volume of the chamber. First electrode wire 12 contains multiple conductive extensions 18 which extend far enough into the sample chamber 42 to make contact with the running buffer 55. Ideally, conductive extensions 18 will contact the surface of the running buffer 55 and will not make contact with the gel 53, the sample 44, or conductive extension 16. The distance between the insulated portions of wires 12 and 14 is not critical to electro-elution according to the invention, provided these portions are properly insulated such that they do not allow for transfer of electricity between wires 12 and 14 except within each sample chamber. Thus, if properly insulated, wires 12 and 14 may rest against the connecting portion 48 between chambers and against each other.

An alternative electro-elution apparatus is shown in FIG. 9. The inventive apparatus shown in FIG. 9 contains an alternative straight first electrode wire 12, as shown in FIG. 4 in which conductive portions 15 are interrupted by insulated portions 17. Because the first wire 12 is straight, it must be placed with respect to the elution buffer 55 such that the uninsulated conductive portion of first wire 12 is in contact with buffer 55. This placement, as shown in FIG. 9, allows the insulated portion 17 of wire 12 to rest below the surface of the chamber connecting section 48, e.g., in a groove. Because these insulated portions 17 of wire 12 may lie in the same plane as the surface of buffer 55, they must be securely insulated and fit tightly enough within the groove so as to block the flow of buffer 55 between adjacent sample chambers. Wire 14 is also depicted as a straight wire, as shown in FIG. 1, which extends through the bottom side-walls of each sample chamber and underlies the sample matrix in each chamber. Thus, an electric field will be created, upon electrification of wires 12 and 14, in each sample chamber between the wires.

In operation, the apparatus shown in FIGS. 8 or 9 is operated by turning on a power supply (not shown) to which first and second wires 12, 14, respectively are electrically connected. If, for example, first wire 12 is an anode electrode wire and second wire 14 is a cathode electrode wire, then an electric field will be created between the negatively charged cathode wire and the positively charged anode wire, allowing for flow of electrolytes between the wires. The electric field will then orient the flow of negatively charged biological molecules in the sample matrix 44 towards the anode wire (or conductive extensions), and thus into solution 55. The sample solutions 55 then may be collected for further analysis.

Thus, when the apparatus is in place and power is applied, a biological molecule such as nucleic acid, being negatively charged, is attracted away from the negative electrode and towards the positive electrode. Thus, in FIGS. 8 and 9, the nucleic acid would be attracted towards the top of the sample chamber and into solution 55 in the sample chamber. The nucleic acid will migrate out of the matrix and along the flowpath which is defined by the space between the electrodes within the sample chamber.

Elution of a charged molecule from the sample matrix into the sample buffer is determined by detecting the charged molecule in the sample buffer after electro-elution; for example, elution of a specified DNA sequence may be determined via PCR using appropriate primers. The inability to detect the charged molecule in the sample matrix will confirm quantitative recovery of the eluted molecule.

After an elapsed time of elution, e.g., 5–10 minutes, the power supply is shut off and the electrode wires are removed before the buffer solution containing the eluted sample is removed.

ELECTRO-ELUTION OF NUCLEIC ACID

The inventive electro-elution devices and methods are particularly useful where it is desirable to electro-elute a biological molecule from a large number of individual samples simultaneously. Described below is use of the inventive devices and methods for screening of newborns for genetic and/or infectious diseases. Thus, DNA or RNA may be eluted using the following procedure; e.g., human nucleic acid or nucleic acid from an infectious organism that is co-isolatable with human nucleic acid.

Human genomic DNA, one such biological molecule referred to herein, was electro-eluted simultaneously from numerous individual samples of a dried spot of blood according to the invention as shown in FIG. 5.

Each blood sample was obtained as a heel-stick specimen that had been adsorbed onto filter paper (#903, Schleicher and Schuell). Each specimen was obtained by hospital nursing staff in accordance with procedures established for routine newborn screening (R. George, Specimen Collection for PKU and Hypothyroidism Screening (No. CDC 80-110) Atlanta, U.S. Department of Health and Human Services, Public Health Service, Centers for Disease Control, Laboratory Training and Consultation Division, 1980). A paper punch was then used to punch out individual spots of the dried blood sample; each punched-out spot corresponding to a biological sample as referred to herein. Each sample spot, approximately 6.5 mm in diameter, was then dispensed into one well of a 96-well microtiter dish. Thus, up to 96 samples, including control spots, may be electro-eluted simultaneously using a single microtiter dish format.

The method includes the use of "ghost" filter papers, which are residual to the elutions of antibody and other proteins from the dried blood spot. Thus, one dried blood spot can serve as a specimen for both protein and nucleic acid analysis. One example of the preparation of "ghosts", residual to the current nation-wide universal screening of anonymous newborns for HIV antibody, follows.

200 $\mu$l of elution buffer (HIV ELISA kit, Genetic Systems, Seattle, Wash.) was dispensed into each sample-containing microtiter dish well. The samples were then allowed to sit in the elution buffer overnight at 4 degrees C. During this initial phase of sample treatment, cellular proteins present in the sample, e.g., hemoglobin and cellular debris, leach out of the paper and into the elution buffer. DNA remains on the filter paper (Yourno, Jour. Clin. Micro. 31(5):1364, 1993, hereby incorporated by reference). The buffer was then removed from the sample well and discarded or set aside for protein analysis, leaving a "ghost" spot that includes primarily nucleic acid. Optionally, the ghost may be further washed with water or buffer by means of an ELISA plate washer, found in most clinical laboratories.

An acrylamide gel plug (approximately 8% polyacrylamide, Sigma Corp., in 80 mMTris, pH 9.0, 3 mMNaH$_2$PO$_4$) was then poured into each well of a second microtiter plate, each well also containing a hole through the bottom surface. The gel plug was allowed to harden and the plate containing gel plugs was pre-electro-eluted (i.e., electro-eluted as described below, but prior to placement of the sample ghost) to remove potentially inhibitory substances in the hardened gel plug. The plate containing gel plugs was removed from the apparatus, emptied of buffer, and a ghost was placed on top of a gel plug. The pre-electro-eluted plate containing gel plugs may be re-used, i.e., to electro-elute additional ghost samples. If a microtiter dish containing a membrane barrier is used instead of a dish containing gel plugs, the membrane barrier-containing dish need not be pre-electro-eluted.

125 $\mu$l of electro-elution solution (80 mM Tris, pH 9.0, 3 mM NaH$_2$PO$_4$) was then dispensed into each well over the gel plug and ghost. Reservoir 19, measuring 12.5 cm in length, 10 cm in width and 3.5 cm in depth, was filled with 250 ml of buffer (10 mM Tris, pH 8.3, 3 mM NaH$_2$PO$_4$), a volume sufficient to fill reservoir 19 so as to be horizontally level with the volume of buffer in each individual sample chamber. Lid 21 was positioned such that anode wire 12 contacted solution 55 in each individual sample chamber. Power supply 22 was then turned to 25 volts for 15 minutes during elution, followed by a polarity reversal for 10 seconds. Upon completion of elution, power supply 22 was turned off and lid 21 removed. A multichannel pipetter was then used to recover the individual sample solutions 55 for further analysis.

Approximately 1 $\mu$g of genomic DNA is thus obtainable from a single drop of blood. The genomic DNA may then be analyzed, e.g., using PCR (M. A. Innis et al., eds., *PCR Protocols, A Guide to Methods and Applications,* Academic Press, Inc., Harcourt Brace Jovannovich Pub., NY, 1990) for genetic mutations which are associated or correlated with genetic diseases. Examples of such diseases include but are not limited to those listed in Tables I and II.

*M. A. Innis et al., eds., *PCR Protocols, A Guide to Methods and Applications,* Academic Press, Inc., Harcourt Brace Jovannovich Pub., NY, 1990.
Hepatitis C Virus, Ravaggi@
@PCR Methods and Applications 1:291, 1992

Electro-elution Of Protein

TABLE I

POINT MUTATION CAUSING HUMAN GENETIC DISEASES

| DISEASE | Gene | Mutation Base change | Mutation Amino ac. change | CD | Author | Journal | Vol. | Page | Yr. |
|---|---|---|---|---|---|---|---|---|---|
| ADA Deficiency | ADA | CGG-CAG | Arg-Gln | 101 | Bonthron | JCI | 76 | 894 | 85 |
| Adenylate kinase def. | AK | cCGG-TGG | Arg-Trp | 128 | Matsuura | JBC | 264 | 10148 | 89 |
| Adrenal hyperplasia | CA21HB | CCC-CGC | Pro-Arg | 426 | Hatteson | PNAS | 8 | 45858 | 87 |
| Aldolase A def. | ALDA | GAT-GGT | Asp-Gly | 128 | Kishi | PNAS | 84 | 8623 | 88 |
| Aldolase B def. | ALDB | tGCT-CCT | Ala-Pro | 149 | Cross | Cell | 53 | 881 | 88 |
| Amyloidotic poly. | PALB | cGTG-ATG | Val-Met | 30 | Furuya | JCI | 80 | 1706 | 87 |
| Angioneurotic edema | CII | gCGC-TGC | Arg-Cys | 444 | Skriver | JBC | 264 | 3066 | 89 |
| Antithrombin III Def. | AT3 | CGT-TGT | Arg-Cys | 47 | Duchange | NAR | 14 | 2408 | 86 |
| α1-Antitrypsin def. | PI | GTG-GCG | Val-Ala | 213 | Nukiwa | JBC | 261 | 15989 | 86 |
| APRT deficiency | APRT | ATG-ACG | Met-Thr | 136 | Hidaka | JCI | 81 | 945 | 88 |
| ApoA1 deficiency | APOA1 | GAGc-GAT | Glu-Asp | 120 | Law | JBC | 260 | 12810 | 85 |
| ApoB deficiency | APOB | aCAA-TAA | Gln-Term | 2153 | Hospatta | BBRC | 148 | 279 | 87 |
| ApoE deficiency | APOB | gCGC-TGC | Arg-Cys | 158 | Funke | ClinChem | 32 | 1285 | 86 |
| Diabetes (ins. res.) | INSR | AGGT-AGT | Arg-Ser | 735 | Yoshimasa | Science | 240 | 784 | 88 |
| Diabetes (MODY) | INS | TTC-TCC | Phe-Ser | 24 | Haneda | PNAS | 80 | 6366 | 83 |
| Ehlers-Danlos IV | COLIA3 | gGGT-AGT | Gly-Ser | 790 | Tromp | JBC | 264 | 1349 | 89 |
| Ehlers-Danlos VII | COLIA1 | ATGG-ATA | Met-Ile | 159 | Weil | EmboJ | 8 | 1705 | 89 |
| Elliptocytosis | SPTA1 | AGTg-AGG | Ser-Arg | 39 | Garbarz | Blood | 72S | 41A | 88 |
| Fabry disease | GLA | cCGG-TGG | Arg-Trp | 356 | Berstein | JCI | 83 | 1390 | 89 |
| Factor X deficiency | FX | cCGC-TGC | Arg-Cys | 366 | Jagadees | JCBS | 13 | 291 | 89 |
| Factor XI deficiency | FXI | aGAA-TAA | Glu-Term | 117 | Asakai | PNAS | 86 | 7667 | 89 |
| Gangliosidosis GM2 | HEXB | CGC-CAC | Arg-His | 178 | Ohno | AJHG | 41 | A231 | 87 |
| G6PD deficiency | G6PD | gAAT-GAT | Asn-Asp | 126 | Vulliamy | PNAS | 85 | 5171 | 88 |
| Gaucher's (type 1) | GBA | CGG-CAG | Arg-Gln | 119 | Graves | DNA | 7 | 521 | 88 |
| Gaucher's (type 2) | GBA | CTG-CCG | Leu-Pro | 444 | Tsuji | NEJM | 316 | 570 | 87 |
| Gerstmann-Straeuss | PRP | CCG-CTG | Pro-Leu | 102 | Hsiao | Nature | 338 | 342 | 89 |
| Gyrate Atrophy | OAT | ATGT-ATA | Met-Ile | 1 | Mitchell | JCI | 81 | 630 | 88 |
| Heparin cofactor2def. | HCF2 | CGC-CAC | Arg-His | 189 | Blinder | JBC | 264 | 5128 | 89 |
| HPRT deficiency | HPRT | tCGA-GGA | Arg-Gly | 50 | Wilson | JCI | 72 | 767 | 83 |
| Hypophosphatasia | ALPL | cGCC-ACC | Ala-Thr | 162 | Weiss | PNAS | 84 | 342 | 89 |
| Hypercholesterolemia | LDRL | CCG-CTG | Pro-Leu | 664 | Soutar | PNAS | 86 | 4166 | 89 |
| Hyperproinsulinemia | INS | aCAC-GAC | His-Asp | B10 | Chan | PNAS | 84 | 2194 | 87 |
| Immunoglobulin K def. | IGK | cTGC-GGC | Cys-Gly | 194 | Stavnezer | Science | 230 | 458 | 85 |
| LDLR deficiency | LDLR | TGGc-TGA | Trp-Term | 792 | Lehrman | Cell | 41 | 735 | 85 |
| Leprechaumism | INSR | gAAG-GAG | Lys-Glu | 460 | Kadowaki | Science | 240 | 787 | 88 |
| Maple syrup urinedis. | BCKD | cTAC-AAC | Tyr-Asn | 394 | Zhang | JCI | 83 | 1425 | 89 |
| Osteogen. imperf. | COLIA1 | tGGT-TGT | Glys-Cys | 748 | Vogel | JBC | 262 | 14737 | 87 |
| OTC deficiency | OTC | CGA-CAA | Arg-Gln | 109 | Maddelena | JCI | 82 | 1353 | 88 |
| Phenylketonuria | PAH | tCGG-TGG | Arg-Trp | 408 | Dilella | Nature | 327 | 333 | 87 |
| Porphyria | UROD | GGG-GAG | Gly-Glu | 281 | DeVerne | Science | 234 | 732 | 86 |
| Protein C def. | PROC | cCGA-TGA | Arg-Term | 306 | Romeo | PNAS | 84 | 2829 | 87 |
| PNP deficiency | NP | tGAA-AAA | Glu-Lys | 89 | Williams | JBC | 262 | 2332 | 87 |
| Rickets (vit. D resist) | VDR | CGA-CAA | Arg-Gln | — | Hughes | Science | 242 | 1702 | 89 |
| Tay-Sachs disease | HEXB | CGC-CAC | Arg-His | 178 | Ohno | J Nchem | 50 | 316 | 88 |
| TPI deficiency | TPI | GAGt-GAC | Glu-Asp | 104 | Daar | PNAS | 83 | 7903 | 86 |
| TSH deficiency | TSHB | tGGA-AGA | Gly-Arg | 29 | Hayashiz | EmboJ | 8 | 2291 | 89 |
| von Willebrand 2a | VWF | GTC-GAC | Val-Asp | 844 | Ginsburg | PNAS | 86 | 3723 | 89 |

Abbreviations used in Table I:
ADA-adenosine deaminase; AJHG-Am, J. Hum, Genet.; Apo-apolipoprotein; APRT-densosinephosphoribosyltrasferase; BBRC-Biochem, Bioshys, Res. comm.; CD-codon; G6PD-glucose-6-phophate dehdrogenase; HPRT-hypoxanthinephosphoribosyltransferase; JBC-J. Biol. Chem.; JCI-J. Clin, Invest.; JCBS-I. Cell. Biol. [Suppl]; J. Nchem-J. Neurochem; LDLR-low density lipoprotein receptor; MBM-Mol. Biol. Med.; MODY-maturity-onset diabetes of the young;
NAR-Nucl. Acids. Res.; NEJM-New Eng. J. Med.; NIDDM-non-insulin-dependent diabetes mellitus; OTC-ornithine transcarbamylase; PNAS-Proc. Natl. Acad. Sci. USA; PNP-purine nucleoside phosphorylase; TPI- triose phosphate isomerase; TSH-thyroid stimulating hormone

TABLE II

Examples of Human Infectious Diseases

Human T-cell Lymphoma/Leukemia Viruses, Ehrlich, G. D. et al.*
Human Immunodeficiency Virus, Kellogg and Kwok*
Hepatitis B Virus, Baginski, I.*
Human Papilloma Virus, Ting*
Human Cytomegalovirus, Shibata*
Human Enteroviruses, Rotbart*

Electro-elution of proteins may be performed according to the invention using the inventive apparatuses described herein. Standard protein electro-elution conditions are described in Ausubel et al., eds., *Current Protocols in Molecular Biology,* Vol. 2, Chap. 10.5.1, Arley & Sons, NY, the contents of which are hereby incorporated by reference.

Genetic Screening

Eluates prepared according to the invention may be useful for any analysis known in the art. For example, where the eluate contains eluted genomic DNA, as described above, the invention provides an eluted molecule which is particularly useful for genetic screening. The DNA may be analyzed for the presence or absence of a particular nucleic acid sequence, i.e., a deletion, insertion, point mutation or exogenous nucleic acid (see Tables I and II).

1. Preparation of DNA for Genetic Screening.

Typically, the eluted DNA is amplified, e.g., using PCR, prior to analysis. Such methods of analysis include, but are not limited to the following: (1) polymerase chain reaction (PCR) followed by sizing gel electrophoresis or hybridization with an allele-specific (or sequence-specific) probe; (2) hybridization of the eluted DNA with a nucleic acid probe that is complementary to the gene or mutated sequence; (3) allele-specific oligonucleotide (ASO) PCR followed by an amplification-detection system (e.g., gel electrophoresis and staining or HPLC); and (4) nucleotide sequencing.

An example of analysis method (1) follows. Typically, the eluted DNA is amplified, e.g., using PCR, prior to analysis. Specific conditions for any one PCR, i.e. a PCR targeting a particular sequence, or for any one multiplex PCR, i.e. a PCR targeting a particular set of sequences, may vary but will be known to a person of ordinary skill in the art.

The DNA present in the electro-elution eluate (i.e., solution 55 after electro-elution) may be placed directly into a PCR assay. Alternatively, for PCR assays that require a change in buffer, the electro-eluted DNA may be "cleaned" prior to PCR, using any one of the many methods known in the art.

Amplification of HLA sequences can be accomplished directly from an aliquot of the 125 $\mu$l electro-elution eluate as follows. 25 $\mu$l of electro-elution eluate is aliquotted into a reaction tube containing 25 $\mu$l H$_2$O, 50 $\mu$l HLA master mix (see below), 0.5 $\mu$l Amplitaq (Perkin Elmer Cetus, Norwalk, Conn.) and 0.5 $\mu$l UNG (Perkin Elmer Cetus, Norwalk, Conn.). A 50 $\mu$l HLAmaster mix comprises 20 mM Tris HCl, pH 8.3, 100 mM KCl, 5 mMMgCl$_2$, 0.02 $\mu$moles each of dATP, dGTP, dCTP, 0.04 $\mu$moles of dUTP, 20 pmoles each of HLADQA primers GH26 and GH27 (Perkin Elmer Cetus, Norwalk, Conn.), and 25 $\mu$g gelatin.

A 242 bp fragment characteristic of HLAamplification can then be visualized under ultraviolet light after ethidium bromide staining a 13% polyacrylamide gel in which an aliquot of the amplification has been electrophoresed. Alternatively, hybridization with allele-specific probes can identify the presence of amplified product from either the normal and/or mutant alleles.

2. Preparation and Detection of Protein for Genetic Screening.

Where the biological molecule to be analyzed is a protein, it may be desireable to release the nucleic acid from sample cells prior to protein elution, or to remove nucleic acid from the sample eluate prior to protein analysis. Thus, the sample or eluate may first be treated to release or remove the nucleic acid by mechanical disruption (such as freeze/thaw, abrasion, sonication), physical/chemical disruption, such as treatment with detergents (e.g., Triton, Tween, or sodium dodecylsulfate), osmotic shock, heat, enzymatic lysis (lysozyme, proteinase K, pepsin, etc.), or nuclease treatment, all according to conventional methods well known in the art.

Where an eluate prepared according to the invention includes a protein, the presence or absence of which is indicative of a genetic disease, the protein may be detected using conventional detection assays, e.g., using protein-specific probes such as an antibody probe. Similarly, where a genetic disease correlates with the presence or absence of an amino acid or sequence of amino acids, these amino acids may be detected using conventional means, e.g., an antibody which is specific for the native or mutant sequence (see Table I for examples of such sequences).

Any of the antibody reagents useful in the method of the present invention may comprise whole antibodies, antibody fragments, polyfunctional antibody aggregates, or in general any substance comprising one or more specific binding sites from an antibody. The antibody may be of any immunoglobulin isotype, e.g., IgG, IgM, and so forth. Any antigen-binding fragment of any such antibody can also be employed, for instance, the Fab' or F(ab')$_2$ fragments. In addition, aggregates, polymers, derivatives and conjugates of immunoglobulins or their fragments can be used where appropriate.

The immunoglobulin source for an antibody reagent can be obtained in any manner such as by preparation of a conventional polyclonal antiserum or by preparation of a monoclonal or a chimeric antibody. Antiserum can be obtained by well-established techniques involving immunization of an animal, such as a mouse, rabbit, guinea pig or goat, with an appropriate immunogen.

Alternatively, sandwich hybridization techniques may be used, e.g., an antibody specific for a fusion protein, for example, $\beta$-galactosidase fused with a protein which is specific for the detectable protein. In addition, an antibody specific a for haptenic group conjugated to the binding protein can be used. Another sandwich detection system useful for detection is the avidin or streptavidin system, where the a protein specific for the detectable protein has been modified by addition of biotin. In yet another embodiment, the antibody may be replaced with a non-immunoglobulin protein which has the property of binding to an immunoglobulin molecule, for example Staphylococcal protein A or Streptococcal protein G, which are well-known in the art. The protein may either itself be detectable labeled or may be detected indirectly by a detectable labeled secondary binding protein, for example, a second antibody specific for the first antibody. Thus, if a rabbit-anti-mismatch-binding protein antibody serves as the first binding protein, a labeled goat-anti-rabbit immunoglobulin antibody would be a second binding protein. In another embodiment, the signal generated by presence of the fusion protein of the mismatch-binding protein is amplified by reaction with a specific antibody for that fusion protein (e.g., an anti-$\beta$-galactosidase antibody) which is detectably labeled. One of ordinary skill in the art can devise without undue experimentation a number of such possible first and second binding protein systems using conventional methods well-known in the art.

Where the first or second binding protein described above is an antibody, detection may be accomplished using any of a variety of conventional immunoassays, including enzyme immunoassays (EIA) (Voller, A., *Diagnotic Horizons* 2:1–7, 1978, Microbiological Associates Quarterly Publication, Walkersville, Md.; Voller, A. et al., *J. Clin. Pathol.* 31:507–520 (1978); U.S. Reissue Pat. No. 31,006; UK Patent 2,019,408; Butler, J. E., *Meth. Enzymol.* 73:482–523 (1981); Maggio, E. (ed.), *Enzyme Immunoassay,* CRC Press, Boca Raton, Fla., 1980) or radioimmunoassays (RIA) (Weintraub, B., *Principles of radioimmunoassays*, Seventh Training Course on Radioligand Assay Techniques, The Endocrine Society, March 1986, pp. 1–5, 46–49 and 68–78).

For example, an antigen-specific antibody or antibody fragment is detectably labeled by linking the same to an enzyme and use it in an EIA, or enzyme-linked immunosorbent assay (ELISA). This enzyme, in turn, when later exposed to a substrate in such a manner as to produce a chemical moiety which can be detected, for example, by spectrophotometric, flourometric or, most preferably, by visual means. The substrate may be a chromogenic substrate which generates a reaction product visible to the naked eye.

Enzymes which can be used to detectably label the binding protein which is specific for the desired detectable protein, include, but are not limited to, alkaline phosphatase, horseradish peroxidase, glucose-6-phosphate dehydrogenase, staphylococcal nuclease, delta-V-steroid isomerase, yeast alcohol dehydrogenase, alpha-glycerophosphate dehydrogenase, triose phosphate isomerase, asparaginase, ribonuclease, urease, catalase, glucose-6-phosphate dehydrogenase, glucoamylase and acetylcholinesterase.

By radioactively labeling the binding protein, for example, the antibody, it is possible to detect the antigen bound to a solid support through the use of a radioimmunoassay (RIA). The radioactive isotope can be detected by such means as the use of a gamma counter or a scintillation counter or by autoradiography. Isotopes which are particularly useful for the purpose of the present invention are: $^3H$, $^{131}I$, $^{14}C$, and preferably $^{125}I$.

It is also possible to label the first or second binding protein with a fluorescent compound. When the flourescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The first or second binding protein also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the first or second binding protein. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Other Embodiments

The invention is not limited to those embodiments described herein, but may encompass modifications and variations which do not depart from the spirit of the invention. While the invention has been described in connection with specific embodiments thereof, it will be understood that further modifications are within the scope of the invention. For example, the first electrode wire may be adapted to attach to the underside of a plastic lid which fits over the plural sample chambers in order to insulate the user and to provide a cover for the device while in electrical operation. The invention is intended to cover any variations, uses, or adaptations which fall within the scope of the following claims, including such departures from the present disclosure as come within known or customary practice within the art to which the invention pertains, and as may be applied to the essential features hereinbefore set forth as follows in the scope of the appended claims. Other embodiments are within the following claims.

I claim:

1. An electro-elution apparatus comprising
   plural sample chambers, each sample chamber containing an eluant solution;
   an anode wire and a cathode wire, wherein one of said anode or cathode wires comprises a plurality of serially connected conductive extensions, and each said conductive extension extends into a corresponding sample chamber, and
   wherein each said sample chamber defines a flow path for flow of electrolytes between said cathode and anode wires, wherein said plural sample chambers are simultaneously accessible for simultaneous removal of said eluant solutions.

2. The electro-elution apparatus of claim 1, further comprising a buffer reservoir for containing said plural sample chambers, wherein each said sample chamber comprises upper and lower portions, said lower portion comprising barrier means for allowing electrolyte flow but preventing liquid exchange between each said chamber and said reservoir.

3. The electro-elution apparatus of claim 2 wherein said anode wire comprises said plurality of serially connected conductive extensions for extending into each corresponding sample chamber, and said cathode wire extends into said buffer reservoir.

4. A method of electro-elution, comprising
   providing plural electric fields using the apparatus of claim 1 and corresponding plural individual sample matrices; and
   simultaneously electro-eluting a charged molecule from each of said plural individual sample matrices into each of corresponding plural individual sample eluants.

5. The method of claim 4, further comprising
   simultaneously recovering said plural individual sample eluants.

6. An electro-elution apparatus comprising
   an anode wire comprising a plurality of serially connected conductive extensions,
   a cathode wire, and
   a plurality of sample chambers and a buffer reservoir, wherein each said anode wire conductive extension extends into a sample chamber and said cathode wire extends into said buffer reservoir,
   wherein each said sample chamber defines a flow path for flow of electrolytes between said cathode wire and each said anode wire conductive extension.

7. The apparatus of claim 6 wherein said sample chamber comprises
   upper and lower portions, said lower portion comprising barrier means for allowing electrolyte flow but preventing liquid exchange between each said sample chamber and said buffer reservoir.

8. The apparatus of claim 7 wherein each said sample chamber defines an internal volume of less than 500 $\mu l$.

9. The apparatus of claim 7, further comprising a power supply to which said anode wire and said cathode wire electrically connect.

10. The apparatus of claim 7, further comprising insulated handle means for placing said anode wire such that said anode wire conductive extensions are extendable into sample chambers.

11. The apparatus of claim 10, said insulated handle means comprising a cover to which said anode wire is structurally attached.

12. The apparatus of claim 6, further comprising insulating means cooperative with said anode wire to insulate said anode wire between any two consecutive serially connected conductive extensions of said plurality of serially connected conductive extensions.

13. A method of electro-elution, comprising electro-eluting a negatively charged molecule from each of plural individual sample matrices via corresponding plural electric fields comprising an electrified anode wire comprising a plurality of serially connected conductive extensions and an electrified cathode wire, wherein each said electric field extends from a single conductive anode extension and said cathode wire.

14. A method of electro-elution, comprising the steps of
(a) providing an apparatus comprising an anode wire comprising a plurality of serially connected conductive extensions and a cathode wire;
(b) placing each of plural sample matrices containing a biological molecule between each said conductive anode extension and said cathode wire; and
(c) providing electricity to said apparatus for a time and under buffer conditions sufficient to simultaneously elute said biological molecule from each said sample matrix to form a sample eluate containing said biological molecule.

15. The method of claim 14, further comprising
(d) collecting said plural sample eluates.

16. An electro-elution method comprising the steps of
(a) providing an electro-elution apparatus comprising a cathode wire extending into a buffer reservoir, an anode wire comprising a plurality of serially connected conductive extensions, and a corresponding plurality of sample chambers, each sample chamber containing an eluant solution, wherein each said anode wire conductive extension is extendable into a said eluant solution and each said sample chamber defines a flow path for flow of electrolytes between said cathode wire in said buffer reservoir and each said anode wire conductive extensions;
(b) placing each of a plurality of sample matrices containing a biological molecule to be eluted into each of said corresponding plurality of sample chambers;
(c) providing sufficient electricity to said anode and cathode wires to elute said biological molecule from each said plural samples into said eluant solution.

17. An electro-elution apparatus comprising
first and second electrode wires, wherein said second wire comprises a plurality of serial conductive extensions, each said conductive extension being shaped so as to substantially conform to the internal shape of a sample chamber, wherein, upon electrification, said first and second wires are cooperable with a plurality of sample chambers simultaneously to define a plurality of electric fields.

18. An electro-elution apparatus comprising
(a) first and second electrode wires, each said wire including a plurality of conductive extensions, wherein said first and second wires cooperate to form a plurality of pairs of conductive extensions, each pair comprising a first wire conductive extension and a corresponding second wire conductive extension spaced apart so as to define a flowpath in conductive medium for the flow of ions; and
(b) a plurality of sample chambers, wherein the members of each said pair of conductive extensions extend into a sample chamber.

19. The apparatus of claim 17 wherein said first electrode wire further comprises plural conductive extensions.

20. The apparatus of claim 17 or 18 wherein said first or second electrode wires further comprises insulating material wrapped around the wire between said conductive extensions.

21. The apparatus of claim 18 wherein said second electrode wire is shaped such that each said second wire conductive extension conforms to the internal shape of each said sample chamber.

22. The apparatus of claim 17 or 18 wherein each said first electrode wire is shaped such that each said first wire conductive extension is extendable into a sample chamber without contacting said second wire conductive extension.

23. The apparatus of claim 17, further comprising a plurality of sample chambers.

24. The apparatus of claim 17 or 18, wherein at least one of said first and second electrode wires is insulatively adapted so as to allow manual movement of said wire.

25. An electro-elution kit comprising
(a) the apparatus of claim 1, 2, 3, 6, or 18, and
(b) packaging material therefore.

26. A method of electro-eluting a biological molecule from a sample matrix, comprising
(b) providing an electro-elution apparatus comprising first and second electrode wires electrically connected to an electric power source, wherein at least said second electrode wire includes plural conductive extensions;
(a) providing plural sample chambers, each said chamber containing a sample matrix comprising said biological molecule and electro-elution buffer solution;
(c) placing said first and second wires such that each said conductive extension of said second wire extends into a sample chamber of said plural sample chambers, said first and second wires being spaced apart so as to define a flow path for ions upon electrification; and
(d) electro-eluting said biological molecule by imposing an electric field within each said sample chamber between said first and second wires sufficient to elute said biological molecule from said sample matrix into said buffer solution.

27. A method of electro-eluting a biological molecule from a sample matrix, comprising the steps of:
(a) providing the apparatus of claim 18 and a plurality of sample chambers, each said chamber containing a sample matrix comprising a biological molecule and a conductive buffer solution, wherein each said conductive extension of said second electrode wire is immersed in said solution within said sample chamber;

(b) electro-eluting said biological molecule from said sample matrix by imposing an electric field within each said sample chamber between said first and second electrode wires sufficient to elute said biological molecule from said sample matrix into said buffer.

28. A method of electro-eluting a biological molecule from a sample matrix, comprising the steps of:
  (a) providing the apparatus of claim 18, wherein each said sample chamber further comprises a sample matrix containing said biological molecule and conductive medium;
  (b) electro-eluting said biological molecule from said sample matrix by imposing an electric field within each said sample chamber between said first and second electrode wires sufficient to elute said biological molecule along said flowpath from said sample matrix into said buffer.

29. The method of any of claims 26, 27, or 28 wherein said eluted biological molecule is selected from the group consisting of nucleic acid, protein, and carbohydrate.

30. The method of any of claims 26, 27, or 28 wherein each said sample chamber provided in step (a) has an internal volume of less than 500 $\mu$l.

31. The method of claim 30 wherein each said sample chamber provided in step (a) has an internal volume of less than 250 $\mu$l.

32. The method of claim 31 wherein each said sample chamber provided in step (a) has an internal volume of less than 100 $\mu$l.

33. The method of any of claims 26, 27, or 28 wherein said eluted biological molecule in each said sample chamber comprises less than 50 $\mu$g.

34. The method of claim 39 wherein said biological molecule eluted in said electro-eluting step in each said sample chamber comprises less than 10 $\mu$g.

35. The method of claim 34 wherein said biological molecule eluted in step (d) in each said sample chamber comprises less than 2 $\mu$g.

* * * * *